Figure 1:
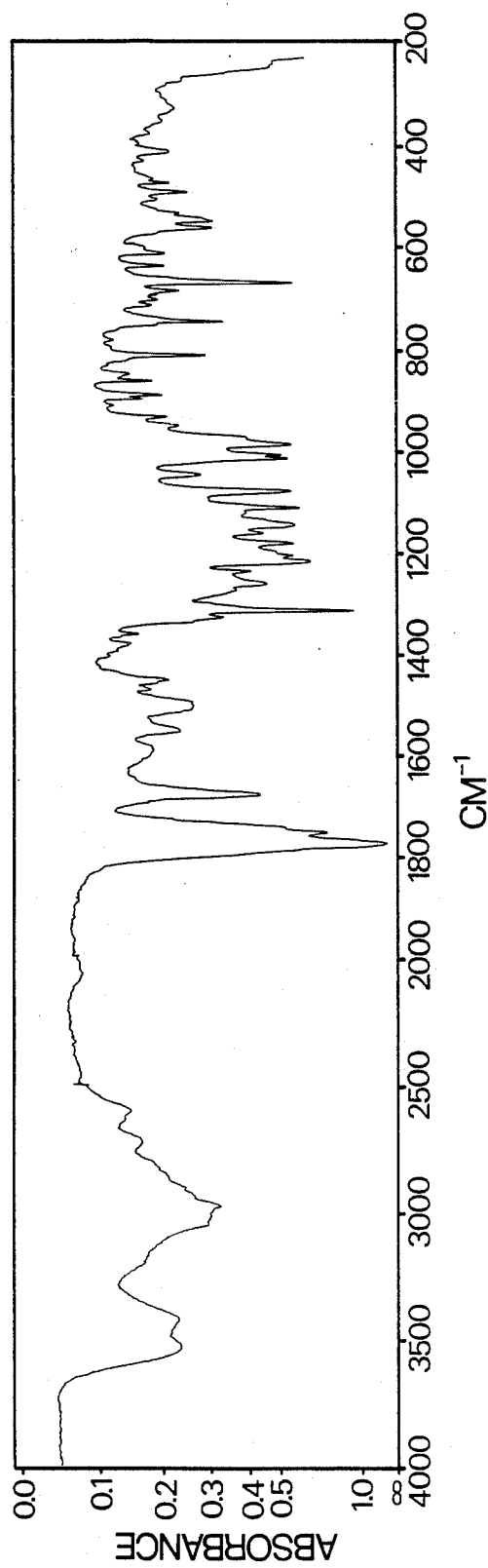

United States Patent [19]

Godtfredsen et al.

[11] Patent Number: 4,882,325

[45] Date of Patent: Nov. 21, 1989

[54] CRYSTALLINE 1,1-DIOXOPENICILLANOYLOXYMETHYL 6-(D-AMINO-PHENYLACETAMIDO)-PENICILLANATE NAPSYLATE AND METHOD OF USING THE SAME

[75] Inventors: Wagn O. Godtfredsen, Vaerlose; Welf von Daehne, Rungsted Kyst, both of Denmark

[73] Assignee: Leo Pharmaceutical Products Ltd. A/S, Ballerup, Denmark

[21] Appl. No.: 262,150

[22] Filed: Oct. 21, 1988

Related U.S. Application Data

[63] Continuation of Ser. No. 304,050, Sep. 21, 1981, abandoned.

[30] Foreign Application Priority Data

Oct. 6, 1980 [GB] United Kingdom ................ 8032147

[51] Int. Cl.$^4$ ................ A61K 31/43; C07D 499/32; C07D 499/22
[52] U.S. Cl. ................ 514/195; 540/320; 540/336
[58] Field of Search ................ 540/314, 333, 336; 514/195

[56] References Cited

U.S. PATENT DOCUMENTS

| | | | |
|---|---|---|---|
| 3,180,862 | 4/1965 | Silvestri et al. | 540/336 |
| 3,674,776 | 7/1972 | Long et al. | 540/336 |
| 4,244,951 | 1/1981 | Bigham | 514/195 |

FOREIGN PATENT DOCUMENTS 881675 8/1980 Belgium .

*Primary Examiner*—Werren B. Lone
*Assistant Examiner*—Vera C. Clarke
*Attorney, Agent, or Firm*—Cushman, Darby & Cushman

[57] ABSTRACT

Crystalline 1,1-dioxopenicillanoyloxymethyl 6-(D-α-amino-α-phenylacetamido)penicillanate napsylate. The product may be prepared by reacting 1,1-dioxopenicillanoyloxymethyl 6-(D-α-amino-α-phenylacetamido)-penicillanate or a salt thereof with 2-naphthalenesulfonic acid or salt thereof.

3 Claims, 1 Drawing Sheet

CRYSTALLINE 1,1-DIOXOPENICILLANOYLOXYMETHYL 6-(D-AMINO-PHENYLACETAMIDO)PENICILLANATE NAPSYLATE AND METHOD OF USING THE SAME

This is a continuation of applicaion Ser. No. 06/304,050, filed Sept. 21, 1981, which was abandoned upon the filing hereof.

SUMMARY

The present invention relates to a new salt of the antimicrobial agent 1,1-dioxopenicillanoyloxymethyl 6-(D-α-amino-α-phenylacetamido)penicillanate, more particularly the salt with 2-naphthalenesulfonic acid, and in particular this salt in crystalline, hydrated form, preferably the monohydrate.

The salt is easily obtained in a crystalline state devoid of organic solvent residues, it shows good stability on storage, it is effectively absorbed and hydrolyzed in vivo, and it is thus specifically suitable for medical treatment of patients, in particular for oral administration.

The present invention relates to a new salt of the antimicrobial agent 1,1-dioxopenicillanoyloxymethyl 6-(D-α-amino-α-phenylacetamido)penicillanate.

More particularly the invention relates to the 2-naphthalenesulfonate of the above antimicrobial agent, to pharmaceutical compositions containing the salt, to dosage units of such compositions, to methods of treating patients (including animals) with the above salt and compositions thereof, and to methods for the preparation of the salt.

For easy reference 1,1-dioxopenicillanoyloxymethyl 6-(D-α-amino-α-phenylacetamido)penicillanate and its salt with 2-naphthalenesulfonic acid are hereinafter also designated VD 1827 and VD 1827 napsylate, respectively.

The invention comprises the above VD 1827 napsylate in various hydrated forms, of which the crystalline monohydrate is the preferred form.

The preparation, the properties and the use of VD 1827 are disclosed in the Specification to British Patent Application No. 8,002,682.

VD 1827 is an orally active antibiotic intended for the treatment of infectious diseases. It is readily absorbed upon oral administration, and during or after absorption it is hydrolyzed with liberation of ampicillin and the β-lactamase inhibitor penicillanic acid 1,1-dioxide in equimolar amounts, giving rise to high blood and tissue concentrations of the two components concomitantly.

VD 1827 can be prepared e.g. by reacting chloromethyl 6-(D-α-azido-α-phenylacetamido)penicillanate with potassium penicillanate 1,1-dioxide in a first step and in a second step the azido group of the reaction product is hydrogenated to form the desired VD 1827.

Other methods are available, e.g. methods in which iodomethyl penicillanate 1,1-dioxide is reacted with a salt of ampicillin with a temporarily protected amino group in which method the last step comprises removing the protecting group.

Certain salts of VD 1827, such as the hydrochloride, have a tendency to form solvates with organic solvents which may be disadvantageous, among other things from a stability point of view. Certain other salts may be difficult to obtain in a crystalline state.

In contrast hereto, the VD 1827 napsylate is easily obtained in the crystalline state devoid of organic solvent residues. It has further been found that the salt shows good stability on storage.

VD 1827 is, as well as 2-naphthalenesulfonic acid, a non-toxic compound, and thus the salt according to the invention is specifically suitable for medical treatment of patients, in particular for oral administration.

The efficient absorption and in vivo hydrolysis of the VD 1827 napsylate monohydrate were shown in a study in human volunteers. The results of the study are summarized below:

Urinary excretion in 0 to 24 hours of ampicillin (A) and penicillanic acid 1,1-dioxide (B) in healthy volunteers, following oral administration of 235 mg of VD 1827 napsylate monohydrate (corresponding to 100 mg of anhydrous ampicillin and 67 mg of penicillanic acid 1,1-dioxide) in aqueous suspension.

| | Urinary excretion (% of dose) | | | | | | | | | |
|---|---|---|---|---|---|---|---|---|---|---|
| | 0–3 hours | | 3–6 hours | | 6–12 hours | | 12–24 hours | | 0–24 hours | |
| Subject | A | B | A | B | A | B | A | B | A | B |
| WOG | 37 | 43.2 | 9 | 8.8 | 2.9 | 6.0 | 0.2 | 1.6 | 49.1 | 60.1 |
| VD | 24 | 15.6 | 28 | 30.6 | 3.1 | 5.6 | 0.5 | 9.3 | 55.6 | 61.1 |
| KH | 33 | 55.7 | 17 | 22.0 | 3.0 | 5.4 | 0.2 | 1.4 | 53.2 | 84.6 |
| SV | 17 | 21.9 | 35 | 45.6 | 2.8 | 6.4 | 0.3 | 1.3 | 55.1 | 75.2 |
| Mean | | | | | | | | | 53.3 | 70.3 |

It is also an advantage that pharmaceutical compositions tailored for sustained release effect and containing the slightly soluble VD 1827 napsylate can give rise to controlled release of VD 1827 over a considerable period of time, but still resulting in sufficiently high blood levels of the VD 1827 components witha view to combating the bacteria causing the infection.

It is a further advantage that the salt of the invention is deprived of the unpleasant taste of the soluble salts of VD 1827 and has therefore proved to be very suitable in the preparation of specific pharmaceutical forms of presentation such as suspensions, which are often used in the pediatric practice.

Due to its physico-chemical properties, VD 1827 napsylate has also proved appropriate with a view to a commercial scale manufacture.

VD 1827 napsylate can be prepared by known methods for salt formation. In one embodiment the new salt is prepared by reacting the free 2-naphthalenesulfonic acid with VD 1827 in a suitable medium with a view to accomplishing the desired reaction.

In another embodiment the VD 1827 napsylate can be prepared in a single or double decomposition, e.g. by reacting the hydrochloride of VD 1827 with the free 2-naphthalenesulfonic acid or its salts, e.g. with alkali metals or organic bases.

In general the salt of the invention can be produced by known methods for producing salts. Accordingly, the primary conditions are that protonized VD B 1827 is brought together with 2-naphthalenesulfonate ions in a suitable medium with a view to obtaining the VD 1827 napsylate directly as a precipitate, or indirectly by in a first step removing the by-product of the reaction, e.g. potassium chloride, and in a second step recovering the desired salt by evaporation of the solvent and crystallization. Alternatively, it may be precipitated by adding a solvent in which its solubility is low. The experts can easily select the appropriate solvent or mixture of solvents having knowledge of the solubility of VD 1827 napsylate and the solubilities of the starting substances used and by-products formed in the process.

Thus, the solubilities of VD 1827 napsylate monohydrate, are as follows: Very slightly soluble: isopropanol, ethyl acetate, ether, hexane; Slightly soluble: acetone, methanol, ethanol, water; Soluble: dimethylformamide, dimethylsulfoxide.

In a specific embodiment of the invention, VD 1827 napsylate is obtained by adding 2-naphthalenesulfonic acid in the laste step of the synthesis of VD 1827 when removing the amino-protecting group, whereby VD 1827 is readily recovered as its napsylate.

As mentioned hereinbefore the preferred form of VD 1827 napsylate is its crystalline monohydrate form, and consequently its crystallization or precipitation can appropriately take place in a solvent containing a minor amount of water but sufficient to cause formation of the desired monohydrate.

If higher hydrates are intended to be produced the solvent must at least contain the theoretical amount of water.

In a further embodiment, crystalline VD 1827 napsylate can be obtained from the amorphous compound by crystallization from a solvent or a mixture of solvents at least containing the approximate amount of water.

Details of various embodiments will appear from the examples.

It is a further object of the invention to provide pharmaceutical compositions which are useful in the treatment of infectious diseases in the human and veterinary practice, and which may be used for enteral, parenteral or topical administration, but preferably for enteral use.

In the following (except the examples) the designation VD 1827 napsylate is used for the monohydrate.

With this object in view, the compositions of the invention contain as an active component at least VD 1827 napsylate together with solid or liquid pharmaceutical carriers and/or diluents.

In the said compositions, the proportion of therapeutically active material to carrier substance can vary between 1% and 95% by weight. The compositions can be worked up to various pharmaceutical forms of presentation, such as tablets, slow release tablets, effervescent tablets, pills, dragees, suppositories, capsules, ointments, powders, optionally for suspension or reconstitution, suspensions and the like.

Pharmaceutically acceptable, non-toxic, organic or inorganic, solid or liquid carriers and/or diluents can be used to make up compositions containing the present compounds. Gelatine, lactose, starch, magnesium stearate, talc, vegetable and animal fats and oils, gum, polyalkylene glycol, buffers or other known carriers, auxiliary agents and/or diluents for medicaments are all suitable.

Futhermore, the compositions may contain other therapeutically active components which can appropriately be administered together with the VD 1827 napsylate in the treatment of infectious diseases, such as other antibacterials, antitussives, pain-relieving drugs, probenecid, etc. In particular, antibacterials, which act synergistically with one or both of the active components formed by in vivo hydrolysis of the VD 1827 napsylate, are appropriate. Such compounded compositions may e.g. be administered in the form of multilayer tablets or core tablets.

As indicated above, the present compounds may be worked up to pharmaceutical forms of presentation including suspensions and non-aqueous ointments. A pharmaceutical preparation for oral treatment may be in the form of a suspension of VD 1827 napsylate, the preparation containing from 10 mg to 100 mg per ml of the vehicle.

Another object of the invention resides in the selection of a dose of the VD 1827 napsylate and a dosage unit of the compositions of the invention which dose and dosage unit can be administered so that the desired activity is achieved without simultaneous secondary effects. In the human therapy the present compounds are conveniently administered (to adults) in dosage units of the compositions containing not less than 50 mg and up to 2500 mg, preferably from 100 mg to 1000 mg calculated as the VD 1827 napsylate.

By the term "dosage unit" is meant a unitary, i.e. a single dose which is capable of being administered to a patient, and which may be readily handled and packed, remaining as a physically stable unit dose comprising either the active material as such or a mixture of it with solid or liquid pharmaceutical diluents, carriers, solvents and/or auxiliary agents.

In the form of a dosage unit, the VD 1827 napsylate may be administered once or more times a day at appropriate intervals, always depending, however, on the condition of the patient, and in accordance with the prescription made by the medical practitioner.

Thus a daily dose will typically be an amount of from 0.25 to 15 g of VD 1827 napsylate, which conveniently can be divided into several single doses.

In the continuous therapy of patients suffering from infectious diseases, the tablets, or suspensions are the appropriate forms of pharmaceutical preparations, if desired in the form of sustained-release formulations of tablets.

In the veterinary practice the above pharmaceutical compositions may also be used, preferably in the form of dosage units containing from 50 mg up to 25 g of VD 1827 napsylate.

For the treatment of mammary disorders, especially bovine mastitis, the antibacterial agent can be administered by the intramammary route in liquid or semiliquid form, such as an ointment, or together with a substantially water-insoluble and oil-insoluble binding agent in the form of granules. In compounded mastitis formulations, penethamate, or its hydroiodide, is an appropriate component.

Still another object of the invention is to provide a method of treating patients suffering from infectious diseases, the method comprising administering to adult patients an effective amount of VD 1827 napsylate, preferably in the form of the dosage units aforesaid. The VD 1827 napsylate is typically administered in amounts of 3–200 mg/kg body weight of the patient/day, preferably in amounts of 7–70 mg/kg body of the patient/day, corresponding to, for adult human patients, from 0.25 g to 15 g per day, or preferably from 0.5 g to 5 g per day.

In the treatment of patients, the present compounds can be administered either alone or together with other therapeutically active compounds, e.g. probenacid, which aid in combating the bacterial infection. Such combined treatment can be performed with formulations containing more or all of the therapeutically active compounds, or these may be administered in separate formulations, these being given simultaneously or with suitable intervals.

In the treatment of patients, the daily dose is administered either at one time, or in divided dosages, e.g., two, three or four times a day.

The invention will be further described in the following Examples which are not to be construed as limiting the invention.

EXAMPLE 1

VD 1827 napsylate monohydrate

VD 1827 hydrochloride (63.1 g, 0.1 mole) was dissolved in a mixture of water (400 ml) and dimethylformamide (100 ml). A solution of sodium 2-naphthalenesulfonate (23.0 g, 0.1 mole) in water (500 ml) was added dropwise with stirring. The crystalline precipitate was collected after stirring for 1 hour at ambient temperature, washed with water and dried in vacuo to yield the title compound as colourless crystals.

The dried product was treated with 96% ethanol (5 ml/g) at 40° C., whereby a clear solution was obtained. Crystallization was induced by scratching, and the mixture was cooled to ambient temperature and left for 1 hour. The crystals were filtered off, washed with ethanol (1 ml/g), and dried to constant weight in vacuo to give the title compound as colourless crystals with m.p. 170°–72° C. (decomposition). $[\alpha]_D^{20}$ +173° (c=1, methanol).

Found: C, 51.21; H, 4.97; N, 6.82; S, 11.68 and $H_2O$, 2.20%. $C_{35}H_{38}N_4O_{12}S_3$, $H_2O$ requires C, 51.21; H, 4.91; N, 6.82; S, 11.72 and $H_2O$, 2.19%.

The IR-spectrum (KBr) showed strong bands at 1780, 1760, 1745, 1685, 1515, 1320 and 680 $cm^{-1}$ (confer FIG. 1).

The NMR-spectrum [$(CD_3)_2SO$] showed signals at $\delta$=1.36 (s, 6H), 1.47 (s, 6H), 3.2–3.9 (m, 2H), 4.43 (s, 1H), 4.53 (s, 1H), 5.1–5.2 (m, 2H), 5.42 (d, J=4, 1H), ~5.6 (dd, 1H), 5.91 (bs, 2H), 7.4–8.2 (m, 12H), 8.65 (b, 3H), and 9.4 (d, 1H) ppm. Tetramethylsilane was used as internal reference.

EXAMPLE 2

VD 1827 napsylate monohydrate

To a cold (+5° C.) solution of VD 1827 hydrochloride (6.3 g, 0.01 mole) in water (50 ml), ethyl acetate (50 ml) was added, followed by 1M aqueous potassium hydrogen-carbonate (10 ml). The organic phase was separated, and a 0.5M solution of 2-naphthalenesulfonic acid in ethyl acetate (20 ml) was added. The clear solution was stirred and shortly crystallized. The product was filtered off after stirring for 1 hour at ambient temperature, washed with ethyl acetate, and dried in vacuo to give the title compound as colourless crystals which after recrystallization from ethanol had m.p. 170°–72° C. (decomposition).

EXAMPLE 3

VD 1827 napsylate monohydrate

To a stirred solution of VD 1827 hydrochloride (6.3 g, 0.01 mole) in water (50 ml), ethyl acetate (25 ml) was added, followed by dropwise addition of 1N aqueous 2-naphthalenesulfonic acid (10 ml). After stirring for 1 hour at ambient temperature the crystalline precipitate was filtered off, washed successively with water and ethyl acetate and dried in vacuo to furnish the napsylate monohydrate as colourless crystals which after recrystallization from ethanol had m.p. 170°–72° C. (decomposition).

EXAMPLE 4

Preparation of VD 1827 and its napsylate monohydrate

To a stirred, cooled (+5° C.) mixture of 6β-(D-α-amino-α-phenylacetamido)-penicillanic acid trihydrate (40.4 g) and tetrabutylammonium hydrogensulfate (34.0 g) in water (100 ml) and dichloromethane (200 ml), 4N aqueous sodium hydroxide (50 ml) was added slowly. The two clear layers were separated, and the aqueous phase was extracted with dichloromethane (100+50 ml). The combined dichloromethane layers were dried ($MgSO_4$) and evaporated in vacuo to an oil. The oil was dissolved in ethyl acetate (500 ml), and residual dichloromethane was removed in vacuo. A cold (+5° C.) solution of iodomethyl penicillanate 1,1-dioxide (38 g) in ethyl acetate (200 ml) was added in one portion, and the mixture was stirred for 5 minutes at +5° C. The separated tetrabutylammonium iodide was filtered off, and the filtrate was immediately stirred with a cold (+5° C.) mixture of water (200 ml) and 1N hydrochloric acid (100 ml). The aqueous phase was separated, and ethyl acetate (100 ml) was added. Under stirring, a solution of sodium 2-naphthalenesulfonate (23 g) in water (250 ml) was added dropwise in the course of 30 minutes. After addition of about 100 ml of the solution, a crystalline precipitate was formed. The mixture was stirred for an additional 10 minutes, whereafter the crystals were filtered off and washed thoroughly with water (2×50 ml), followed by ethyl acetate (2×50 ml). The product was dried in the air for 24 hours. M.p. 170°–72° C. (decomposition) after recrystallization from ethanol.

EXAMPLE 5

Preparation of VD 1827 and its napsylate monohydrate

Potassium carbonate (16.6 g, 0.12 mole) was suspended in a mixture of dimethylformamide (250 ml) and methyl acetoacetate (23.8 ml, 0.22 mole). Anhydrous ampicillin (38.4 g, 0.11 mole) was added, and the mixture was stirred for 3 hours at ambient temperature, and then for 18 hours at +5° C. Iodomethyl penicillanate 1,1-dioxide (37.3 g, 0.10 mole) was added, and stirring was continued for 20 minutes at 5°–10° C. Ethyl acetate (500 ml) and water (250 ml) were added, and the intermediate, 6β-[N-(1-methoxycarbonylpropen-2-yl)-D-α-amino-α-phenylacetamido]-penicillanoyloxymethyl penicillanate 1,1-dioxide, was hydrolyzed at pH 2.5 at ambient temperature with 1N hydrochloric acid. When the consumption of acid stopped, a solution of sodium 2-naphthalenesulfonate (23 g, 0.10 mole) in water (500 ml) was added. Crystallization was induced by seeding and scratching, and the mixture was stirred for 2 hours at +5° C. The crystals were filtered off, washed with water, followed by ethyl acetate, and dried in vacuo to give the title compound as colourless crystals.

Recrystallization from ethanol was performed as described in Example 1, resulting in the pure product with m.p. 170°–72° C. (decomposition).

EXAMPLE 6

Preparation of VD 1827 and its napsylate monohydrate

To an ice-cooled solution of potassium 6β-[N-(1-methoxycarbonylpropen-2-yl)-D-α-amino-α-phenylacetamido]-penicillanate (13.85 g, 0.027 mol) in dimethylformamide (25 ml), iodomethyl penicillanate 1,1-dioxide (9.33 g, 0.025 mole) was added, and the mixture was stirred for 30 minutes at +5° C. Ethyl acetate (50 ml) and water (75 ml) were added, and the amino-protected intermediate was hydrolyzed at pH 2.5 at ambient temperature with 1N aqueous 2-naphthalenesulfonic acid. The mixture was seeded, and the crystalline product was collected after stirring for 2 hours at +5° C., washed with water followed by ethyl acetate, and dried in vacuo to yield the title compound as colourless crystals.

Recrystallization from ethanol was performed as described in Example 1, resulting in the pure product with m.p. 170°-72° C. (decomposition).

EXAMPLE 7

Powder for aqueous suspension

| Component | Per 100 ml of suspension |
|---|---|
| VD 1827 napsylate monohydrate | 5.00 g |
| Tween 20 | 0.05 g |
| Sucrose | 40.00 g |
| Sodium citrate | 0.60 g |
| Sodium caragheenate | 0.40 g |
| Flavour (q.s.) | |
| | 46.05 g |

The active compound is micronized, the other ingredients are added, and the mixture is carefully blended to obtain a uniform product. From the resulting powder an aqueous suspension is prepared by addition of purified water to a total volume of 100 ml.

EXAMPLE 8

Tablets

| Component | Per tablet |
|---|---|
| VD 1827 napsylate monohydrate | 500 mg |
| Corn starch | 75 mg |
| Methyl cellulose | 5 mg |
| Carboxymethyl starch | 25 mg |
| Magnesium stearate | 5 mg |
| | 610 mg |

The active compound is blended with the corn starch and granulated with a 5% solution of methyl cellulose in deionized water. After drying at 50° C. and screening through 0.75 mm screens, the granules are blended with carboxymethyl starch and magnesium stearate. The resulting mixture is compressed into tablets each weighing 610 mg.

EXAMPLE 9

Capsules

| Component | Per capsule |
|---|---|
| VD 1827 napsylate monohydrate | 250 mg |
| Lactose | 50 mg |
| Methyl cellulose | 2.5 mg |
| Magnesium stearate | 2.5 mg |
| | 305 mg |

The active ingredient and the lactose are granulated with a 5% solution of methyl cellulose in de-ionized water, dried at 50° C., and screened through 1 mm sieves. To the granules is added magnesium stearate, the mixture is carefully blended, and 305 mg of the blend are filled into No. 2 gelatine capsules.

EXAMPLE 10

Veterinary suspension

| | |
|---|---|
| Penethamate hydriodide | 100 g |
| VD 1827 napsylate monohydrate | 100 g |
| 12-Hydroxystearin(x) | 20 g |
| Coconut oil modified(xx) | 780 g |
| | 1000 g |

(x)Trade Mark "THIXIN ®"
(xx)Trade Mark "NEOBEE ®"

12-Hydroxystearin is dissolved in coconut oil at 70° C. and cooled to room temperature. Penethamate hydriodide and VD 1827 napsylate monohydrate are incorporated by agitation followed by homogenization. The suspension is filled into plastic syringes each containing 5 g of the suspension.

EXAMPLE 11

Veterinary suspension

| | |
|---|---|
| Penethamate hydriodide | 20 g |
| VD 1827 napsylate monohydrate | 40 g |
| Framycetin sulfate | 20 g |
| Aluminium monostearate | 20 g |
| 12-Hydroxystearin | 10 g |
| Liquid paraffin | 890 g |
| | 1000 g |

Aluminium monostearate and 12-hydroxystearin are dissolved in liquid paraffin at 130° C. and cooled to 30° C. Penethamate hydriodide, VD 1827 napsylate monohydrate, and framycetin sulfate are incorporated by agitation followed by homogenization. The suspension is filled into plastic syringes each containing 5 g of the suspension.

EXAMPLE 12

Effervescent tablet of VD 1827 napsylate

| Components | |
|---|---|
| VD 1827 napsylate monohydrate | 250 mg |
| Citric acid | 600 mg |
| Sodium hydrogencarbonate | 400 mg |
| Polyethylenglycol 6000 | 20 mg |
| Sodium saccharine | 20 mg |

The powders are premixed, sieved and mixed again. The mixed powders are compressed to tablets.
Tablet weight: 1.290 grams
Punch size: circular, diameter 18 mm, plane surface.

EXAMPLE 13

Tablets

| Components | |
|---|---|
| VD 1827 napsylate monohydrate | 5000 g |
| Corn starch | 750 g |
| Methyl cellulose | 50 g |
| Sodium carboxymethyl starch | 250 g |
| Magnesium stearate | 50 g |
| | 6100 g |

The active compound is blended with the corn starch and granulated with a 5% solution of methyl cellulose in deionized water. After drying at 50° C. and screening through 0.75 mm screens, the granules are blended with sodium carboxymethyl starch and magnesium stearate. The resulting mixture is compressed into tablets each weighing 610 mg.

EXAMPLE 14

Capsule 250 mg

| Components | |
|---|---|
| VD 1827 napsylate monohydrate | 2500 g |
| Poly(vinylpolypyrrolidone)$^{(x)}$ | 250 g |
| Magnesium stearate | 25 g |
| | 2775 g |

$^{(x)}$Plasdone XL ®, GAF

The components are mixed, sieved through a 0.7 mm sieve and filled into gelatine capsules each containing 277.5 mg of the powder mixture.

EXAMPLE 15

Powder for aqueous suspension

| Components | |
|---|---|
| VD 1827 napsylate monohydrate | 2500 g |
| Sucrose | 30000 g |
| Sodium citrate | 250 g |
| Sodium carboxymethylcellulose | 250 g |
| Flavour | q.s. |

The components are sieved through a sieve 0.5 mm, mixed and filled into unit dose sachets each containing 3.3 g of powder, equivalent to 250 mg of VD 1827 napsylate monohydrate.

EXAMPLE 16

Suppository 400 mg

| Components | |
|---|---|
| VD 1827 napsylate monohydrate | 4000 g |
| Hard fat$^{(x)}$ | 21000 g |

$^{(x)}$e.g. Witepsol W 25 ®, Dynamit Nobel

The VD 1827 napsylate monohydrate is sieved through a sieve 0.125 mm and suspended into the melted hard fat not exceeding 40° C. The mixture is dosed into suppository moulds using a suitable suppository machine. Each suppository weighes 2.5 g, equivalent to a content of 400 mg of VD 1827 napsylate monohydrate.

EXAMPLE 17

Intramammary

| Components | |
|---|---|
| VD 1827 napsylate monohydrate | 100 g |
| 12-Hydroxystearin$^{(xx)}$ | 20 g |
| Coconut oil modified$^{(xxx)}$ | 880 g |
| | 1000 g |

$^{(xx)}$Trade Mark "THIXIN ®"
$^{(xxx)}$Trade Mark "NEOBEE ®"

12-Hydroxystearin is dissolved in coconut oil at 70° C. and cooled to room temperature. VD 1827 napsylate is incorporated by agitation followed by homogenization. The suspension is filled into plastic syringes each containing 5 g of the suspension.

EXAMPLE 18

Multilayer tablet

| Each tablet contains | |
|---|---|
| VD 1827 napsylate monohydrate | 250 mg |
| VD 1825$^{(x)}$ hydrochloride | 250 mg |
| Components for granulate A | |
| VD 1827 napsylate monohydrate | 2500 g |
| Corn starch | 375 g |
| Methylcellulose | 25 g |
| Sodium carboxymethyl starch | 125 g |
| Magnesium stearate | 25 g |
| | 3050 g |

$^{(x)}$VD 1825 is 1,1-dioxopenicillanoyloxymethyl 6-[(hexahydro-1H—azepin-1-yl)-methyleneamino]penicillanate.

The VD 1827 napsylate granulate is manufactured as indicated in example 13.

| Components for granulate B | |
|---|---|
| VD 1825$^{(x)}$ hydrochloride | 2500 g |
| Lactose | 520 g |
| Magnesium stearate | 30 g |
| | 3050 g |

$^{(x)}$VD 1825 is 1,1-dioxopenicillanoyloxymethyl 6-[(hexahydro-1H—azepin-1-yl)-methyleneamino]penicillanate.

The components are mixed, compressed into a slugging machine. The slugs are crushed and sieved to a granule size of approximately 1 mm.

The two granules A and B are compressed to multilayer tablets, each layer weighing 305 mg.

EXAMPLE 19

Pediatric tablet

| Each tablet contains | |
|---|---|
| VD 1827 napsylate monohydrate | 250 mg |
| Components | |
| VD 1827 napsylate monohydrate | 2500 g |
| Corn starch | 375 g |
| Methylcellulose | 25 g |
| Sodium carboxymethyl starch | 125 g |
| Magnesium stearate | 25 g |
| | 3050 g |

The tablets are manufactured as described in example 13, each tablet weighing 305 mg.

EXAMPLE 20

Coated granulate

| Each sachet contains | |
|---|---|
| VD 1827 napsylate monohydrate | 500 mg |
| Components | |
| VD 1827 napsylate monohydrate | 5000 g |
| Corn starch | 500 g |
| Methylcellulose | 100 g |
| Hydroxypropylmethylcellulose | 500 g |
| Sucrose | 20000 g |
| Sodium carboxymethylcellulose | 500 g |
| | 26600 g |

VD 1827 napsylate monohydrate and corn starch are mixed and wet granulated wtih methylcellulose dissolved in an appropriate amount of water. The dried granulate is slugged and broken down to granules. Granules of sizes 0.5–0.8 mm are collected by sieving.

Too coarse or too fine granules are reprocessed. The granules are coated in a fluid-bed process with an aqueous solution of hydroxypropylmethyl cellulose. The coated granules are mixed with sucrose and sodium carboxymethylcellulose and filled in sachets, each containing 2.66 grams.

EXAMPLE 21

Tablet

| Each tablet contains | |
| --- | --- |
| VD 1827 napsylate monohydrate | 200 mg |
| Pivmecillinam hydrochloride | 200 mg |
| Components for granulate A | |
| VD 1827 napsylate monohydrate | 2000 g |
| Corn starch | 300 g |
| Methylcellulose | 20 g |
| Sodium carboxymethyl starch | 100 g |
| Magnesium stearate | 20 g |
| | 2440 g |

The VD 1827 napsylate granulate is manufactured as indicated in example 13.

| Components for granulate B | |
| --- | --- |
| Pivmecillinam hydrochloride | 2000 g |
| Lactose | 420 g |
| Magnesium stearate | 20 g |
| | 2440 g |

The compounds are mixed, compressed into a slugging tablet machine. The slugs are crushed and sieved to a granule size of approximately 1 mm.

The two granulates A and B are compressed into two-layer tablets, each layer weighing 244 mg.

EXAMPLE 22

Tablet

| Each tablet contains | |
| --- | --- |
| VD 1827 napsylate monohydrate | 250 mg |
| Pivampicillin | 125 mg |
| Components | |
| VD 1827 napsylate monohydrate | 2500 g |
| Pivampicillin | 1250 g |
| Povidone$^{(x)}$ | 250 g |
| Microcrystalline cellulose | 2000 g |
| Magnesium stearate | 60 g |
| | 6060 g |

$^{(x)}$Povidone = 1-vinyl-2-pyrrolidinone polymers

The components are sieved through a sieve 0.7 mm, mixed and compressed using a slugging tablet machine. The slugs are crushed and sieved to a granule size of approximately 1 mm.

The granulate are compressed to tablets each weighing 606 mg.

What we claim is:

1. Crystalline 1,1-dioxopenicillanoyloxymethyl 6-(D-α-amino-α-phenylacetamido)penicillanate napsylate monohydrate.

2. An antibacterial composition, comprising as an active ingredient, an antibacterially effective amount of the compound according to claim 1 together with a pharmaceutically acceptable, non-toxic carrier therefor.

3. A method of treating patients suffering from bacterial infectious diseases which comprises the administration of an effective amount of a compound according to claim 1.

* * * * *